US011497712B2

(12) United States Patent
Stein et al.

(10) Patent No.: US 11,497,712 B2
(45) Date of Patent: Nov. 15, 2022

(54) METHOD OF PREPARING A PHARMACEUTICAL COMPOSITION

(71) Applicant: KINDEVA DRUG DELIVERY L.P., Saint Paul, MN (US)

(72) Inventors: Stephen W. Stein, Lino Lakes, MN (US); David W. Schultz, Pine Springs, MN (US); John K. Simons, Davie, FL (US); William F. Hansen, Riverfalls, WI (US)

(73) Assignee: Kindeva Drug Delivery L.P., St. Paul, MN (US)

( * ) Notice: Subject to any disclaimer, the term of this patent is extended or adjusted under 35 U.S.C. 154(b) by 0 days.

(21) Appl. No.: 16/282,411

(22) Filed: Feb. 22, 2019

(65) Prior Publication Data

US 2019/0183784 A1 Jun. 20, 2019

Related U.S. Application Data

(63) Continuation of application No. 15/324,377, filed as application No. PCT/US2015/042429 on Jul. 28, 2015, now abandoned.

(Continued)

(51) Int. Cl.
*A61K 9/00* (2006.01)
*A61K 47/10* (2017.01)
(Continued)

(52) U.S. Cl.
CPC ............ *A61K 9/008* (2013.01); *A61K 9/0007* (2013.01); *A61K 9/1688* (2013.01);
(Continued)

(58) Field of Classification Search
CPC .... A61K 9/008; A61K 9/0007; A61K 9/1688; A61K 31/137; A61K 31/167;
(Continued)

(56) References Cited

U.S. PATENT DOCUMENTS 5,182,097 A   1/1993   Byron et al.
5,492,688 A   2/1996   Bryon et al.
(Continued)

FOREIGN PATENT DOCUMENTS

CA   2 854 258   5/2012
EP   0 518 601   12/1992
(Continued)

OTHER PUBLICATIONS

Errington. 3M [online]; 2012; downloaded from <URL http://multimedia.3m.com/mws/media/11594770/inhalation-mfg-cold-fill-pressure-fill-and-find-rgt-ptnr.pdf > on Apr. 24, 2020; 3 pages. (Year: 2012).*

(Continued)

*Primary Examiner* — David Browe
(74) *Attorney, Agent, or Firm* — Mueting Raasch Group

(57) ABSTRACT

The present disclosure provides a method of preparing a pharmaceutical composition. The method includes transferring a predetermined quantity of an excipient mixture from a second vessel to a first vessel. The excipient mixture transferred from the second vessel includes a liquid-state second quantity of a hydrofluoroalkane propellant and a first solubilized excipient comprising a low-molecular weight poly(ethylene oxide) polymer. The method further includes contacting at least one pharmaceutically-active compound with the excipient mixture under conditions that facilitate forming an intermixture comprising the propellant, the polymer, and the compound. Before transferring the excipient mixture, the first vessel contains a vapor-phase first quantity of the hydrofluoroalkane propellant and an effective amount of the at least one pharmaceutically-active compound.

12 Claims, 2 Drawing Sheets

Related U.S. Application Data

(60) Provisional application No. 62/030,350, filed on Jul. 29, 2014.

(51) Int. Cl.

| | |
|---|---|
| *A61K 47/32* | (2006.01) |
| *A61K 45/06* | (2006.01) |
| *A61K 9/16* | (2006.01) |
| *A61M 15/00* | (2006.01) |
| *A61K 9/46* | (2006.01) |
| *A61K 31/137* | (2006.01) |
| *A61K 31/167* | (2006.01) |
| *A61K 31/58* | (2006.01) |
| *A61K 47/06* | (2006.01) |
| *B65B 31/00* | (2006.01) |

(52) U.S. Cl.
CPC .......... *A61K 31/137* (2013.01); *A61K 31/167* (2013.01); *A61K 31/58* (2013.01); *A61K 45/06* (2013.01); *A61K 47/06* (2013.01); *A61K 47/10* (2013.01); *A61K 47/32* (2013.01); *A61M 15/009* (2013.01); *B65B 31/003* (2013.01)

(58) Field of Classification Search
CPC ........ A61K 31/58; A61K 45/06; A61K 47/06; A61K 47/10; A61K 47/32; A61M 15/009; B65B 31/003
See application file for complete search history.

(56) References Cited

U.S. PATENT DOCUMENTS

| | | | |
|---|---|---|---|
| 5,795,564 | A | 8/1998 | Aberg et al. |
| 6,261,539 | B1 | 7/2001 | Adjei et al. |
| 7,759,328 | B2 | 7/2010 | Govind et al. |
| 8,104,469 | B2 | 1/2012 | Dams |
| 8,143,239 | B2 | 3/2012 | Govind et al. |
| 8,252,268 | B2 | 8/2012 | Slowey et al. |
| 8,414,956 | B2 | 4/2013 | Jinks et al. |
| 8,430,097 | B2 | 4/2013 | Jinks et al. |
| 8,575,137 | B2 | 11/2013 | Govind et al. |
| 8,616,201 | B2 | 12/2013 | Jinks et al. |
| 2004/0208833 | A1 | 10/2004 | Hovey et al. |
| 2005/0089478 | A1* | 4/2005 | Govind .............. A61K 31/167 424/46 |
| 2005/0207984 | A1 | 9/2005 | Oliver et al. |
| 2007/0286814 | A1* | 12/2007 | Sawant ................ A61P 11/06 424/45 |
| 2011/0020244 | A1 | 1/2011 | Flanders et al. |
| 2011/0103330 | A1 | 5/2011 | Montojo et al. |
| 2012/0204871 | A1 | 8/2012 | Vega |
| 2013/0019863 | A1 | 1/2013 | Stevenson et al. |
| 2013/0025592 | A1 | 1/2013 | Bromley-Davenport et al. |
| 2013/0330281 | A1 | 12/2013 | Malhotra et al. |
| 2014/0147393 | A1 | 5/2014 | Malhorta et al. |

FOREIGN PATENT DOCUMENTS

| | | |
|---|---|---|
| WO | WO 1991/11173 | 8/1991 |
| WO | WO 1992/00061 | 1/1992 |
| WO | WO 1993/05765 | 4/1993 |
| WO | WO 1993/11743 | 6/1993 |
| WO | WO 1993/11745 | 6/1993 |
| WO | WO 1998/05302 | 2/1998 |
| WO | WO 1998/21175 | 5/1998 |
| WO | WO 1998/56349 | 12/1998 |
| WO | WO 2001/47493 | 7/2001 |
| WO | WO 2004/069225 | 8/2004 |
| WO | WO 2008/152398 | 12/2008 |

OTHER PUBLICATIONS

European Pharmacopoeia, 5th Ed. vol. 2; 2004; pp. 2289.
Brochure entitled SYMBICORT® 80/4.5—SYMBICORT® 160/4.5 from AstraZeneca; 2012; 14 pgs.
Blondino, F. et al.; "Surfactant Dissolution and Water Solubilization in Chlorine-Free Liququfied Gas Propellants"; Drug Development and Industrial Pharmacy; 1998; pp. 935-945.
Metcalf, S. et al.; "Development and Validation of a Stress Testing Process for Symbicort® Pressurized Metered Dose Inhaler"; Proceedings from Respiratory Drug Delivery; 2008; pp. 387-390.
Paul, A. et al.; "Explaining the phase behavior of the pharmaceutically relevant polymers poly(ethylene glycol) and poly(vinyl pyrrolidone) in semi-fluorinated liquids"; Journal of Pharmacy and Pharmacology; vol. 57; 2005; pp. 973-980.
Robins, E. et al.; "Formulation Development of a Budesonide HFA-MDI"; Proceedings from Respiratory Drug Delivery; 2006; pp. 931-934.
Rogueda, P. et al.; "Particle synergy and aerosol performance in non-aqueous liquid of two combinations metered dose inhalation formulations: An AFM and Raman investigation"; Journal of Colloid and Interface Science; vol. 361; 2011; pp. 649-655.
Traini, D. et al.; "Investigation into the influence of polymeric stabilizing excipients on inter-particulate forces in pressurised metered dose inhalers"; International Journal of Pharmaceutics: vol. 320; 2006; pp. 58-63.

* cited by examiner

METHOD OF PREPARING A PHARMACEUTICAL COMPOSITION

CROSS REFERENCE TO RELATED APPLICATIONS

This application is a continuation of U.S. application Ser. No. 15/324,377, filed Jan. 6, 2017, which is a national stage filing under 35 U.S.C. 371 of PCT/US2015/042429, filed Jul. 28, 2015, which claims the benefit of U.S. Provisional Application No. 62/030350, filed Jul. 29, 2014, the disclosures of which are incorporated by reference in their entirety herein.

BACKGROUND

Pressurized metered dose inhalers (MDIs) are widely used devices for the delivery of medicaments to the respiratory tract by inhalation via the oral and nasal routes. Though MDIs are used primarily for topical delivery of drugs to the respiratory tract for treatment of such diseases as asthma and chronic obstructive pulmonary disease (COPD), there is increasing interest in their use for systemic drug delivery. Classes of medicaments commonly delivered by MDIs include bronchodilators (e.g. beta-agonists and anticholinergics), corticosteroids, and anti-allergies.

MDI compositions are comprised of at least a medicament and a propellant, but the MDI compositions may further comprise one or more excipients other than propellant.

MDI compositions are generally characterized as either solutions or suspensions. A solution composition comprises the medicament dissolved or solubilized in propellant or in a mixture of propellant and one or more excipients. A suspension composition contains the medicament in the form of particles which are dispersed in the propellant or in a mixture of propellant and one or more other excipients.

Hydrofluroalkane (HFA) propellants, particularly 1,1,1,2-tetrafluoroethane (HFA-134a) and 1,1,1,2,3,3,3-heptafluoropropane (HFA-227), are currently favored for respiratory drug delivery. Other alternatives to CFCs have been proposed, including dimethyl ether and low molecular weight hydrocarbons, such as propane and butane.

The efficiency of an aerosol device, such as an MDI, is a function of the dose deposited at the appropriate site in the respiratory tract. Deposition is affected by several factors including, for example, the aerodynamic particle size. The distribution of aerodynamic particle sizes of solid particles and/or droplets in an aerosol can be characterized by their mass median aerodynamic diameter (MMAD, the diameter around which the mass aerodynamic diameters are distributed equally) and geometric standard deviation (GSD, the measure of variability of the aerodynamic particle diameters).

For inhalation therapy targeting the lungs, there is a preference for aerosols in which the particles for inhalation have an MMAD of about 0.5 to 10 µm, more preferably about 0.5 to 5 µm, and most preferably about 0.5 to 3 µm. Particles larger than about 5 µm in diameter are primarily deposited by inertial impaction in the oropharynx, particles of about 0.5 to 5 µm in diameter are ideal for deposition in the conducting airways, and particles of about 0.5 to 3 µm in diameter are desirable for aerosol delivery to the lung periphery.

Methods are known in the art for the preparation of suspension aerosol compositions for MDIs. The known methods generally comprise the mixing of preformed medicament powders, which are of a size suitable for inhalation therapy, with propellant and optionally one or more other excipients. Control of the particle size distribution of the aerosol particles generated from the suspension aerosol composition is accomplished primarily via control of the particle size distribution of the medicament powders used to prepare the composition. Thus, considerable care is normally taken to avoid dissolution of the medicament powder in the excipients, as any dissolution of the medicament powder during manufacture of the composition would result in loss of particle size control. Conventional methods for generating medicament powders suitable for preparation of compositions for inhalation therapy, such as suspension aerosol compositions for MDIs, include milling (micronization), spray drying, and supercritical fluid recrystallization.

Suspension aerosol compositions are known in the art and examples of such compositions are disclosed in WO 04/069225, EP 518601, U.S. Pat. No. 5,182,097, WO 93/11743, WO 93/11745, WO 98/05302, U.S. Pat. No. 6,261,539, EP 920302, WO 93/05765, WO 92/00061, EP 513127 and WO 01/47493; which are all incorporated by reference in their entirety.

The conventional processes of MDI manufacture are generally characterized as either "pressure filling" or "cold filling". In pressure filling, the powdered medicament, optionally combined with one or more excipients, is placed in a suitable aerosol container capable of withstanding the vapor pressure of the propellant and fitted with a metering valve. The propellant is then forced as a liquid through the valve into the container. In an alternate process of pressure filling, the particulate drug is combined in a process vessel with propellant and optionally one or more excipients, and the resulting drug suspension is transferred through the metering valve fitted to a suitable MDI container. In cold filling; the powdered medicament, propellant which is chilled below its boiling point and, optionally, one or more excipients; are added to the MDI container. In addition, a metering valve is fitted to the container. For both pressure filling and cold filling processes, additional steps; such as mixing, sonication, and homogenization; are often advantageously included.

The dose limits of aerosol medication delivered to the patient must consistently meet the specifications claimed by the manufacturer and comply with the strict requirements of the regulatory authorities.

SUMMARY

It is now known that processes used to form a mixture comprising hydrofluoroalkane propellant, at least one pharmaceutically-active compound, and a solubilized excipient (e.g., a low-molecular weight poly(ethylene oxide) polymer) can be improved by dissolving the solubilized excipient in the propellant before contacting the propellant with the at least one pharmaceutically-active compound. The inventive process of the present disclosure facilitates rapid suspension of the at least one pharmaceutically-active compound in the propellant.

In one aspect, the present disclosure provides a method of preparing a pharmaceutical composition. The method can comprise transferring a predetermined quantity of an excipient mixture from a second vessel to a first vessel, wherein the excipient mixture transferred from the second vessel comprises a liquid-state second quantity of a hydrofluoroalkane propellant and a first solubilized excipient; and contacting at least one pharmaceutically-active compound with the excipient mixture under conditions that facilitate forming an intermixture comprising the propellant, the solubilized excipient, and the compound. The first solubilized excipient can be a low-molecular weight poly(ethylene oxide) polymer. Before transferring the excipient mixture, the first vessel can contain a vapor-phase first quantity of the hydrofluoroalkane propellant and an effective amount of the at least one pharmaceutically-active compound.

In any embodiment, before transferring the excipient mixture, the first vessel can be substantially free of liquid-state propellant in fluid contact with the at least one pharmaceutically-active compound. In any of the above embodiments, the excipient mixture further can comprise a second solubilized excipient. In any of the above embodiments, the at least one pharmaceutically-active compound can be selected from a group consisting of formoterol fumarate and hydrates thereof, budesonide, fluticasone propionate, fluticasone furoate, salmeterol xinafoate, mometasone furoate, albuterol sulfate, beclomethasone, ipratropium bromide, tiotropium bromide, ciclesonide, indacaterol, vilanterol, glycopyrrolate, generally long acting beta agonists, steroids, long acting muscarinic agonists, and a combination of any of the foregoing pharmaceutically-active compounds.

In any of the above embodiments, the at least one pharmaceutically-active compound comprises a combination of two compounds (e.g., a corticosteroid and a long-acting beta agonist.

In any of the above embodiments, transferring a predetermined quantity of an excipient mixture from a second vessel to a first vessel can comprise placing the first and second vessels in fluid communication. While the first and second vessels are in fluid communication, the first vessel has a first internal pressure and the second vessel has a second internal pressure and the first internal pressure is not more than about 140 kPa below the second internal pressure.

In any of the above embodiments, the method further can comprise transferring a predefined mass of the intermixture or the pharmaceutical composition to a vessel that is configured to be used in a metered-dose inhaler.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

The term "excipient mixture", as used herein, refers to a composition that includes one or more excipient compound solubilized (e.g., dissolved) in a liquid-state, pharmaceutically-acceptable propellant.

The term "propellant" as used herein, means one or more pharmacologically inert liquids or gases which exert a vapor pressure at room temperature sufficient to propel a medicament from a container (e.g., a canister) to a patient upon actuation of a valve (e.g., a metering valve).

The term "pharmaceutical composition", as used herein, refers to a mixture comprising at least one pharmaceutically-active compound, at least one solubilized excipient, and a propellant; each at a concentration that is pharmacologically suitable for delivery to a patient from a metered-dose inhaler.

As used herein, "a," "an," "the," "at least one," and "one or more" are used interchangeably. Thus, for example, "a" metered dose inhaler can be interpreted to mean "one or more" metered dose inhalers.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

DETAILED DESCRIPTION

Figure 1:
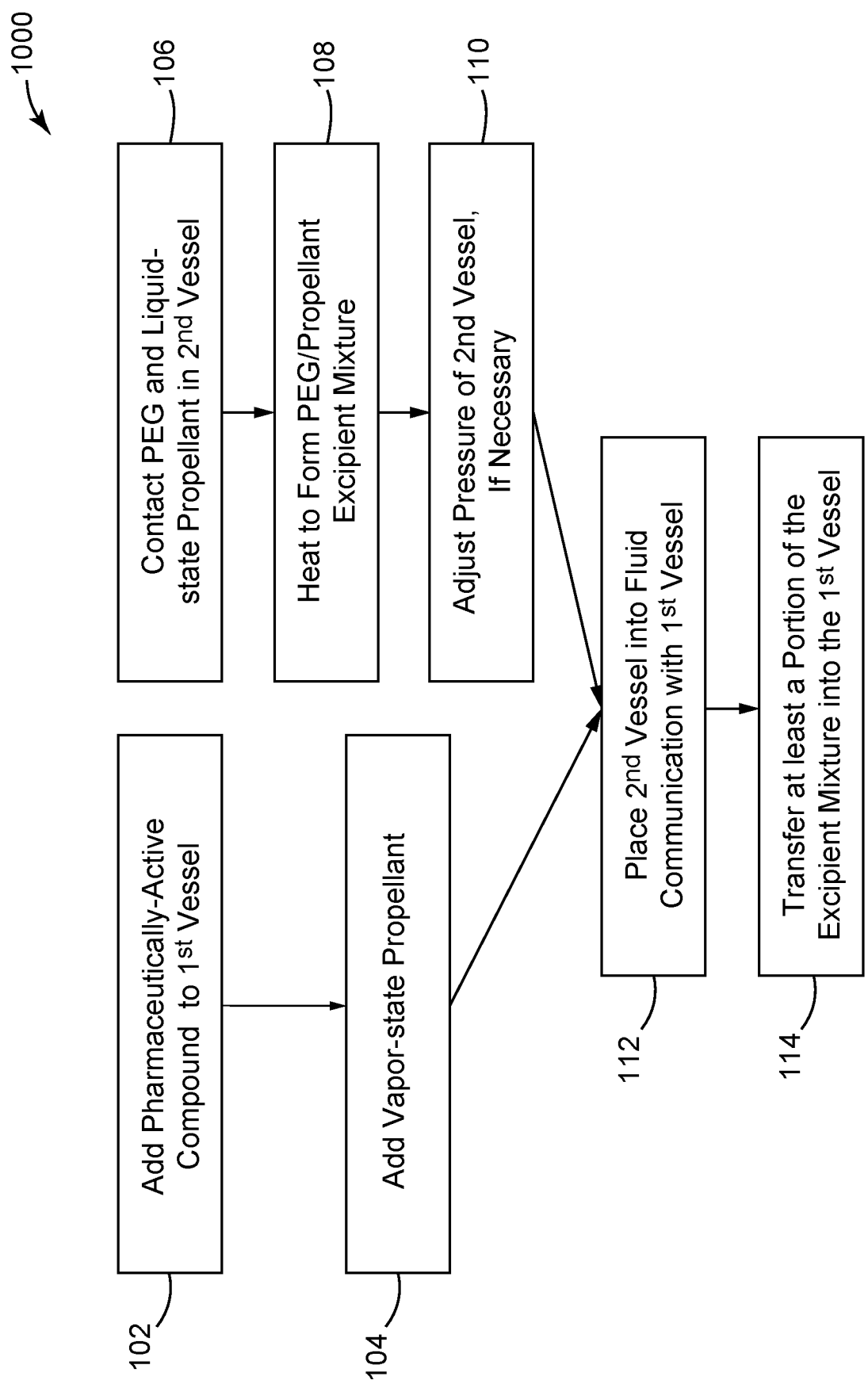
FIG. 1 is a block diagram of one embodiment of a method according to the present disclosure.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. It is to be understood that other embodiments may be utilized and structural or logical changes may be made without departing from the scope of the present disclosure.

The present disclosure provides a method. The method can be used to manufacture a pharmaceutical composition that is used in a metered-dose inhaler device. The pharmaceutical composition can comprise a pharmaceutically-acceptable propellant (e.g., a hydrofluoroalkane propellant), at least one pharmaceutically-active agent, and at least one solubilized excipient. The at least one solubilized excipient functions to facilitate suspension of the at least one pharmaceutically-active compound in the propellant, to lubricate the valve, and/or to manipulate the aerodynamic properties of the delivered aerosol. A poly(ethylene oxide) polymer is one example of a suitable solubilized excipient according to the present disclosure.

As used herein, a poly(ethylene oxide) polymer (PEG polymer) is a compound comprising one or more —$(CH_2CH_2O)_n$— recurring units, wherein n is an integer ≥5. For example, in any embodiment, n is ~6, ~8, ~20, ~25, ~50, or ~75. Preferred PEG polymers are linear. Most preferably the PEG polymer is polyethylene glycol (PEG), i.e. HO—$(CH_2CH_2O)_n$—H. In any embodiment, the weight average molecular weight of the PEG polymer is about 200 to about 3000 Da. In any other embodiment, the weight average molecular weight of the PEG polymer is about 800 to about 2000 Da. In any embodiment, the weight average molecular weight of the PEG polymer is about 1000.

The at least one pharmaceutically-active agent can be an agent that is delivered into the body in the form of particles. The particles of the pharmaceutically-active agent are generally micronized particles or particles processed by other methods known in the art. In any embodiment, the particles can have a mass median diameter equal to or greater than 1 micron. In any embodiment, the particles can have a mass median diameter from about 1 micron to about 5 microns or from about 1 micron to about 10 microns. Smaller particles having a mass median diameter of less than one micron may also be suitable.

In any embodiment, the at least one pharmaceutically-active agent can be selected from a group of pharmaceutically-active agents that are suitable for suspending in a hydroxyfluoroalkane propellant and are capable of being delivered into a body using a metered dose inhaler. Non-limiting examples of suitable pharmaceutically-active agents include formoterol fumarate and hydrates thereof, budesonide, fluticasone propionate, fluticasone furoate, salmeterol xinafoate, mometasone furoate, albuterol sulfate, beclomethasone, ipratropium bromide, tiotropium bromide, ciclesonide, indacaterol, generally long acting beta agonist, steroids, long acting muscarinic agonists, and a combination of any of the foregoing pharmaceutically-active compounds.

Processes of the present disclosure include the use of formoterol as a pharmaceutically-active compound. As would be appreciated by the skilled person, formoterol includes two asymmetric centers, and mometasone contains several asymmetric centers. The present disclosure includes the use of each isomer of formoterol either in substantially pure form or admixed in any proportions or a racemic mixture, particularly the (R,R)-isomer. The enantiomers of formoterol have been described previously, for example, in WO 98/21175 and U.S. Pat. No. 5,795,564.

The use of pharmaceutically-active agents (e.g., formoterol) in a process according to the present disclosure includes the use of suitable salts of the pharmaceutically-active agents. Suitable salts include, for example, those formed with both organic and inorganic acids. Pharmaceutical acceptable acid addition salts include but are not limited to those formed from hydrochloric, hydrobromic, sulphuric, citric, tartaric, phosphoric, lactic, pyruvic, acetic, trifluoroacetic, succinic, oxalic, fumaric, maleic, oxaloacetic, methanesulphonic, ethanesulphonic, p-toluenesulphonic, benzenesulphonic, isethionic, and naphthalenecarboxylic, such as 1-hydroxy-2-naphthalenecarboxylic acids.

Pharmaceutically acceptable esters of a pharmaceutically-active agent (e.g., formoterol), for example, may have a hydroxyl group converted to a $C_{1-6}$ alkyl, aryl, aryl $C_{1-6}$ alkyl, hetaryl (such as furanyl) or amino acid ester.

In preferred embodiments of the invention, formoterol fumarate (suitably as in the form of the dihydrate) is combined with budesonide.

Hereinafter, the term "formoterol" is understood to include formoterol or a pharmaceutical acceptable salt, solvate, or physiologically functional derivative thereof. By the term "physiologically functional derivative" is meant a chemical derivative of formoterol having the same physiological function as the free compound, for example, by being convertible in the body thereto. According to the present invention, examples of physiologically functional derivatives include esters.

Processes of the present disclosure include the use of at least one solubilized excipient (e.g., a first solubilized excipient such as a poly(ethylene oxide) polymer). The solubilized excipient may be a homopolymer, that is the polymer consists of the same recurring structural units, or it may be a co-polymer, that is the polymer contains recurring units that are not the same.

In any embodiment, a method according to the present disclosure can comprise a second solubilized excipient. Preferred solubilized excipients include recurring structural units containing an amide group, such as polyvinylpyrrolidone, for example.

In general, it has been found that polyvinylpyrrolidones having a wide range of average molecular weights give excellent aerosol pharmaceutical compositions, in particular suspensions. Particularly preferred embodiments of the invention are when the second solubilized excipient is polyvinylpyrrolidone (PVP), also known as povidone. Different types of PVP may be characterized by their viscosity in solution, expressed as a K-value (see European Pharmacopoeia, 5th ed., 2004, vol. 2, page 2289). Preferably the K-value of the PVP used is between 10 and 150, more preferably between 15 and 80, more preferably between 20 and 40, most preferably about 25. Suitable polyvinylpyrrolidones are PVP(K25), PVP(K30), Povidone K30, PVP (K29/32), PVP(K90), PVP(K120), PVP (C15), PVP(C30) or PVP/17PF.

In any embodiment, the second solubilized excipient is a co-polymer of vinyl acetate and vinyl pyrrolidone.

Alternative solubilized excipients also include those containing carboxylic acid ester containing recurring structural units such as polyvinyl acetate and co-polymers of vinyl acetate and vinyl pyrrolidone, e.g. polyvinylpyrrolidone/vinyl acetate co-polymer.

In any embodiment of the present disclosure, the aerosol pharmaceutical composition may comprise at least one pharmaceutically-active compound; HFA-134a, HFA-227, or mixtures thereof; and a PEG polymer; wherein said composition contains no alcoholic co-solvent. Preferably said composition contains no polar protic co-solvent, more preferably said composition contains no polar co-solvent.

In any embodiment of the present disclosure, the aerosol pharmaceutical composition may comprise at least one pharmaceutically-active compound; HFA-134a, HFA-227, or mixtures thereof; a PEG polymer; and polyvinylpyrrolidone; wherein said composition contains no alcoholic co-solvent. Preferably said composition contains no polar protic co-solvent, more preferably said composition contains no polar co-solvent.

In any embodiment of the present disclosure, the aerosol pharmaceutical composition may comprise fluticasone or a pharmaceutically acceptable derivative thereof, a hydrofluoroalkane and a PEG polymer. In any embodiment said composition contains no alcoholic co-solvent, preferably no polar protic co-solvent, more preferably no polar co-solvent. Preferably said composition contains only fluticasone or a pharmaceutically acceptable derivative thereof, a hydrofluoroalkane, a PEG polymer; and optionally one or more other pharmacologically active agents e.g., budesonide). Alternatively, preferably said composition contains only fluticasone or a pharmaceutically acceptable derivative thereof, a hydrofluoroalkane, a PEG polymer and, optionally, one or more other pharmacologically active agents (e.g., budesonide).

The amount of PEG polymer (first solubilized excipient) in a pharmaceutical composition made according to the present disclosure will depend on the active ingredient to be dispersed, the concentration of the active ingredient and the particular polymer selected. However, in general the amount of PEG polymer in the pharmaceutical composition is from 0.01 to 5 weight % of the pharmaceutical composition (i.e., the composition that is used to fill the canisters of a metered dose inhaler) made according to the method of the present the present disclosure, more preferably the amount of PEG polymer in the pharmaceutical composition is about 0.01 to about 1.0 weight %.

The amount of second solubilized excipient (e.g., PVP) in a pharmaceutical composition made according to the present disclosure will depend on the active ingredient to be dispersed, the concentration of the active ingredient and the particular polymer selected. However, in general the amount of PVP is from 0.0001 to 1 weight % of the pharmaceutical composition (i.e., the composition that is used to fill the canisters of a metered dose inhaler) made according to the method of the present the present disclosure, more preferably the amount of PVP in the pharmaceutical composition is about 0.0005 to 0.1

Pharmaceutical compositions made according to the present disclosure comprise a propellant. Preferably, the propellant will be a weak solvent or a non-solvent for the medicament; most preferably, the propellant will be a non-solvent for the medicament. Suitable propellants include, for example, hydrofluoroalkanes such as 1,1,1,2-tetrafluoroethane ($CF_3CH_2F$) (HFA-134a) and 1,1,1,2,3,3,3-heptafluoropropane ($CF_3CHFCF_3$) (HFA-227), perfluoroethane, monochloro-difluoromethane, 1,1-difluoroethane (HFA-152a), tetrafluoromethane (PFC-14), trifluoromethane (HFA-23), difluoromethane (HFA-32), fluoromethane (HFA-41), 1,1,2,2,2-pentafluoroethane (HFA-125), 1,1,2,2-tetrafluoroethane (HFA-134), decafluorobutane ($CF_3CF_2CF_2CF_3$); dialkyl ethers such as dimethyl ether; and low molecular weight hydrocarbons such as n-butane, isobutane, propane, and 1,3,3,3-tetrafluoropropene (HFO-1234ze). Propellants may be used singly or in combination. Preferably, the propellant is in a substantially liquid state as it is mixed with the at least one pharmaceutically-active compound and/or the one or more excipients that are solubilized in the propellant. The propellant may be used in a non-supercritical state.

Preferably the propellant used in the method of the present disclosure is HFA-227 or HFA-134a or mixtures thereof, but most preferably it is HFA-227.

The present disclosure provides a method. The method can be used to prepare a pharmaceutical composition that is used in a metered-dose inhaler device. The method involves the use of a plurality of vessels. Each vessel may be any suitable vessel for holding a quantity of propellant that is used in the pharmaceutical composition. The propellant used to make a pharmaceutical composition according to the present disclosure comprises a hydrofluoroalkane propellant (e.g., HFA-227, HFA-134A, or mixtures thereof) known in the art for use in a metered-dose inhaler device.

The method includes a step that involves transferring at least a portion of the contents of one vessel to another vessel. FIG. 1 shows a block diagram of one embodiment of a method 1000 according to the present disclosure.

Prior to the transferring step described below, a first vessel contains a vapor-state first quantity of a hydrofluoroalkane propellant (e.g., HFA-227, HFA-134A, or mixtures thereof) and an effective amount of at least one pharmaceutically-active compound (e.g., at least one of the pharmaceutically-active compounds suitable for distributing (e.g., suspending) in a hydroxyfluoroalkane propellant and capable of being delivered into a body using a metered dose inhaler, as described herein). Thus, in any embodiment, a method according to the present disclosure comprises adding the at least one pharmaceutically-active compound to the first vessel, as shown in step 102 of the method 1000 of FIG. 1. In any embodiment, prior to the transferring step described below, the at least one pharmaceutically-active compound in the first vessel is not in fluid contact with propellant.

The method further comprises adding the vapor-state first quantity of hydrofluoroalkane propellant to the first vessel, as shown in step 104 of the method 1000 of FIG. 1. Preferably, prior to the transferring step described below, the first vessel is substantially free of liquid-state propellant in fluid contact with the at least one pharmaceutically-active compound. "Substantially free of liquid-state propellant", as used herein means that less than 5%, less than 4%, less than 3%, less than 2%, less than 1%, less than 0.5%, or 0% of the mass of the liquid-state propellant used to make the intermixture according to the present disclosure is in fluid contact with the at least one pharmaceutically-active compound.

In any embodiment, the effective amount of the at least one pharmaceutically-active compound is in the form of particles as described herein. In any embodiment, the particles can be substantially insoluble in the propellant and/or in a solubilized low-molecular weight poly(ethylene oxide) polymer and/or in solubilized polyvinylpyrrolidone or mixtures thereof (i.e., mixtures of the propellant and the solubilized low-molecular weight poly(ethylene oxide) and/or the solubilized polyvinylpyrrolidone). A person having ordinary skill in the art will appreciate that the effective amount of the at least one pharmaceutically-active compound will depend upon certain aspects (e.g., the valve configuration, the propellant, the actuator, the particle size of the at least one pharmaceutically-active compound) of the MDI device that is to be used to deliver the pharmaceutical composition into a body and the amount of pharmaceutically-active compound (i.e., the pharmaceutical dose) that is intended to be dispensed in each metered dose delivered by the MDI device. The selection of the effective amount of the at least one pharmaceutically-active compound in the pharmaceutical composition prepared according to the present disclosure is well within the ambit of a person having ordinary skill in the art.

Also prior to the transferring step described below, the second vessel contains a predetermined quantity of an excipient mixture, wherein the excipient mixture comprises a liquid-state second quantity of the hydrofluoroalkane propellant (e.g., HFA-227, HFA-134A, or mixtures thereof) and a first solubilized excipient (e.g., a low-molecular weight poly(ethylene oxide) polymer). In any embodiment, the excipient mixture comprises an optional second solubilized excipient (e.g., polyvinylpyrrolidone). Thus, in any embodiment, a method according to the present disclosure comprises contacting a liquid-state second quantity of the hydroxyfluoroalkane propellant with a suitable excipient (e.g., low-molecular weight poly(ethylene oxide) polymer) in the second vessel, as shown in step 106 of the method 1000 of FIG. 1

In any embodiment, the liquid-state second quantity of the hydroxyfluoroalkane propellant can be heated before and/or after contacting the propellant with the low-molecular weight poly(ethylene oxide) polymer. Heating the propellant can facilitate melting the low-molecular weight poly(ethylene oxide) polymer and, preferably, formation of a substantially homogeneous excipient mixture. Heating the propellant can comprise heating the propellant to a temperature near or above the melting point of the first solubilized excipient (e.g., a poly(ethylene oxide) polymer) or the second solubilized excipient (e.g., PVP). In any embodiment, contacting a liquid-state second quantity of the hydroxyfluoroalkane propellant with the low-molecular weight poly(ethylene oxide) polymer in the second vessel optionally comprises mixing the excipient mixture comprising the second quantity of the hydroxyfluoroalkane propellant and the low-molecular weight poly(ethylene oxide) polymer.

In any embodiment, the quantity of low-molecular weight poly(ethylene oxide) polymer with which the liquid-state second quantity of the hydrofluoroalkane propellant is contacted can be greater than 0 weight percent (e.g., greater than or equal to 0.01 weight percent, greater than or equal to 0.025 weight percent, greater than or equal to 0.05 weight percent, up to about 1 weight percent, up to about 3 weight percent, up to about 5 weight percent, up to about 10 weight percent, up to about 15 weight percent, up to about 20 weight percent) up to about 25 weight percent of the resulting excipient mixture comprising the of low-molecular weight poly(ethylene oxide) polymer and the liquid-state second quantity of the hydrofluoroalkane propellant. In any embodiment, the quantity of low-molecular weight poly (ethylene oxide) polymer with which the liquid-state second quantity of the hydrofluoroalkane propellant is contacted can be about 0.05 weight percent to about 15 weight percent of the resulting excipient mixture comprising the of low-molecular weight poly(ethylene oxide) polymer and the liquid-state second quantity of the hydrofluoroalkane propellant. In any embodiment, the quantity of low-molecular weight poly(ethylene oxide) polymer with which the liquid-state second quantity of the hydrofluoroalkane propellant is contacted can be about 0.1 weight percent to about 10 weight percent of the resulting excipient mixture comprising the of low-molecular weight poly(ethylene oxide) polymer and the liquid-state second quantity of the hydrofluoroalkane propellant.

A "low-molecular weight poly(ethylene oxide) polymer", as used herein, refers to a poly(ethylene oxide) polymer composition having a weight average molecular weight of about 200 Daltons to about 3000 Daltons. In any embodiment, the low-molecular weight poly(ethylene oxide) polymer can have a weight average molecular weight of about 800 Daltons to about 2000 Daltons. In any embodiment, the low-molecular weight poly(ethylene oxide) polymer can have a weight average molecular weight of about 1000 Daltons.

The second quantity of hydrofluoroalkane propellant is a portion (e.g., <1%, about 1%, about 3%, about 5%, about 10%, about 15%, about 20%, about 25%, about 30%, about 35%, about 40%, about 45%, about 50%, about 55%, about 60%, about 65%, about 70%, about 85%, about 80%, about 85%, about 90%, about 95%, >95%) of the total mass of the hydrofluoroalkane propellant used in the pharmaceutical composition made using the method of the present disclosure.

Optionally, in any embodiment, the second quantity of hydrofluoroalkane propellant can be heated (e.g., in the second vessel) to facilitate dissolution of the solid-state low-molecular weight poly(ethylene oxide) polymer. In any embodiment, the second quantity of propellant can be heated before contacting the low-molecular weight poly(ethylene oxide) polymer with the second quantity of propellant (not shown in FIG. 1) and/or after the low-molecular weight poly(ethylene oxide) polymer is contacted with the second quantity of propellant (as shown in step 108 of the method 1000 of FIG. 1).

In any embodiment, the method comprises transferring the predetermined quantity of the excipient mixture from the second vessel to the first vessel. In any embodiment, internal pressure can be monitored in both the first and second vessels during the transfer. In addition, in any embodiment, the internal pressure can be regulated in at least one of the first and second vessels (as shown in step 110 of the method 1000 of FIG. 1) to ensure the internal pressure of the first vessel is at a pressure that is not more than about 210 kPa, not more than 140 kPa, not more than about 105 kPa, not more than about 70 kPa, or not more than about 35 kPa below the internal pressure of the second vessel. In any embodiment, the pressure in the first and second vessels can be approximately equalized before the transfer. Advantageously, keeping the vessels within a predetermined pressure differential prevents sudden excessive vaporization of propellant from the excipient mixture as it is transferred into the first vessel. Excessive vaporization of liquid-state propellant as it enters the first vessel can result in a rapid temperature drop (e.g., to a temperature where the solubility limit of one or more solubilized excipient is below the concentration of the solubilized excipient in the second quantity of the propellant) that can cause precipitation of at least a portion of the low-molecular weight PEG polymer or other solubilized excipient from the excipient mixture, which could result in a decreased ability to suspend the at least one pharmaceutically-active compound in the pharmaceutical composition.

In any embodiment, the temperature of the first vessel and second vessel can be same immediately prior to transferring the excipient mixture. Alternatively, the temperature of the first vessel and second vessel may be different immediately prior to transferring the excipient mixture. In any embodiment, the temperature of the second vessel immediately prior to transferring the excipient mixture may be higher than the first vessel.

Figure 2:
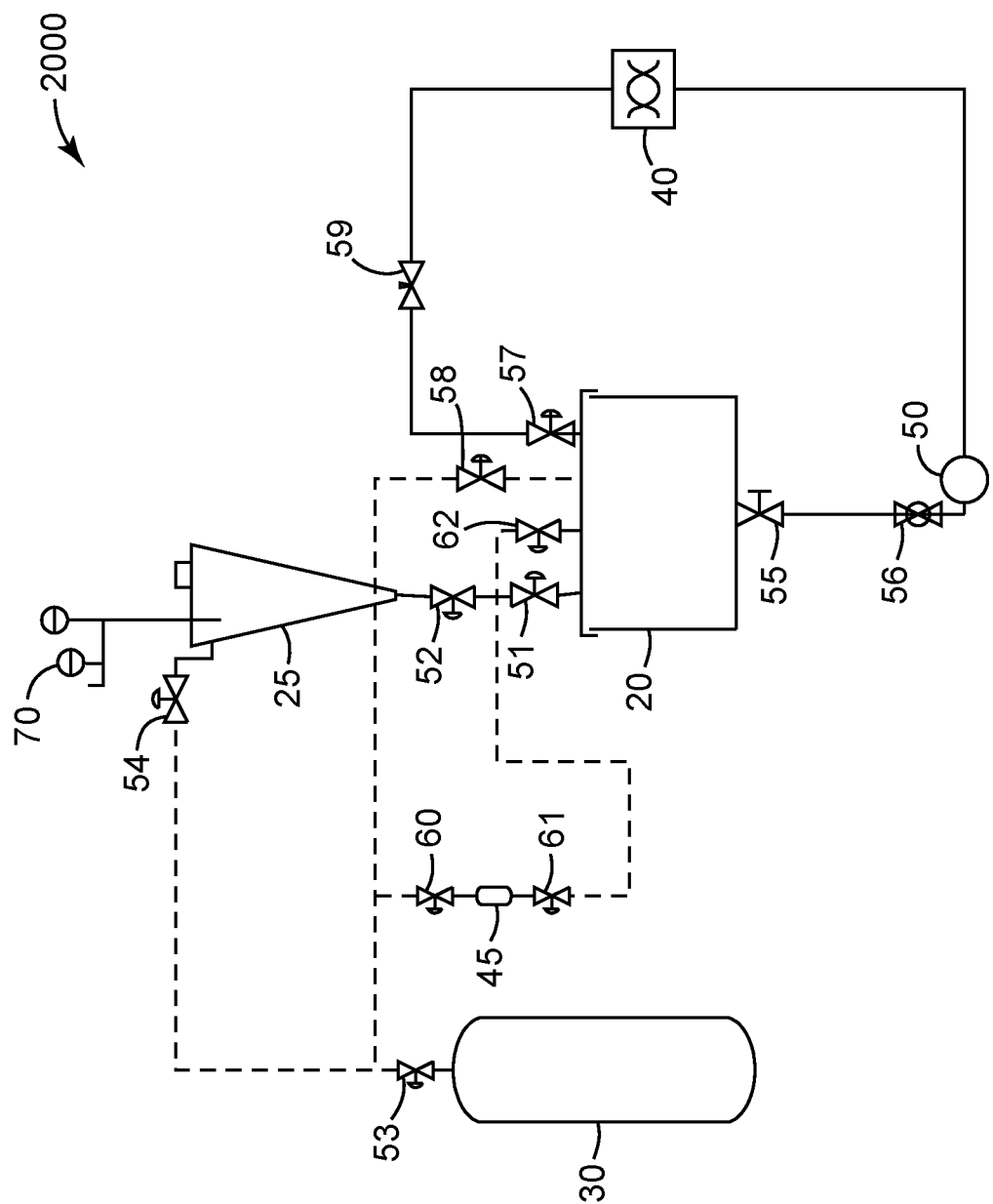
FIG. 2 is a schematic view of one embodiment of process equipment used to practice a method according to the present disclosure.

In order to transfer the predetermined quantity of the excipient mixture from the second vessel to the first vessel, the first vessel and second vessel are placed into fluid communication with each other, as shown in step 112 of the method 1000 of FIG. 1. This can be done, for example, by opening at least one valve that is disposed between the first and second vessels, as shown in FIG. 2.

In any embodiment, prior to transferring the excipient mixture from the second vessel to the first vessel, the first vessel and second vessel are substantially free of an alcoholic co-solvent (e.g., ethanol). "Substantially free of an alcoholic co-solvent", as used herein means that the mass of alcoholic co-solvent in either or both of the first and second vessels is less than 1%, less than 0.5%, less than 0.1%, or 0% of the total mass of the pharmaceutical composition produced by the method of the present disclosure.

In any embodiment, prior to transferring the excipient mixture from the second vessel to the first vessel, the first vessel and second vessel are substantially free of a polar co-solvent (e.g., ethanol, isopropanol). "Substantially free of a polar co-solvent", as used herein means that the mass of polar co-solvent in either or both of the first and second vessels is less than 1%, less than 0.5%, less than 0.1%, or 0% of the total mass of the pharmaceutical composition produced by the method of the present disclosure.

The method further comprises contacting the at least one pharmaceutically-active compound with the excipient mixture under conditions that facilitate forming an intermixture comprising the propellant, the polymer, and the pharmaceutically-active compound, as shown in step 114 of the method 1000 of FIG. 1. Such conditions are known to a person having ordinary skill in the art and may include, for example, heating and/or stirring. In any embodiment, the intermixture can be stirred (e.g., in the first vessel) at a sufficient speed and for a sufficient period of time to obtain a substantially homogeneous mixture of the liquid propellant, the low-molecular weight PEG, and the particles of the at least one pharmaceutically-active compound.

In any embodiment, forming an intermixture comprising the propellant, the polymer, and the pharmaceutically-active compound may comprise forming a pharmaceutical composition. Accordingly, in these embodiments, the intermixture comprises at least one pharmaceutically-active compound, at least one solubilized excipient, and a propellant; each at a first concentration that is pharmacologically suitable for delivery to a patient from a metered-dose inhaler.

Optionally, in any embodiment, the method further comprises mixing a liquid-state third quantity of the hydrofluoroalkane propellant with the intermixture to form a pharmaceutical composition. In these embodiments, the at least one pharmaceutically-active compound and the at least one solubilized excipient of the intermixture are diluted with the liquid-state third quantity of the hydrofluoroalkane propellant to form a pharmaceutical composition wherein the at least one pharmaceutically-active compound, the at least one solubilized excipient, and the propellant each is at a concentration that is pharmacologically suitable for delivery to a patient from a metered-dose inhaler. In these embodiments of the method, the intermixture may or may not be a pharmaceutical composition according to the present disclosure. In the embodiments wherein the intermixture is a first pharmaceutical composition (e.g., a "high-dose" first pharmaceutical composition), the diluted intermixture diluted with addition hydrofluoroalkane propellant is a second pharmaceutical composition (e.g., a "low dose" second pharmaceutical composition).

In any embodiment, the liquid-state third quantity of the hydrofluoroalkane propellant may be added to the intermixture in any suitable vessel (e.g., a relatively large vessel for the preparation of bulk quantities of the pharmaceutical composition (e.g., the second pharmaceutical composition) or a relatively small vessel (e.g., a canister to be used in a metered dose inhaler)).

In any embodiment, a method of the present disclosure further comprises transferring a predefined mass of the pharmaceutical composition to a vessel that is configured to be used in a metered-dose inhaler.

Dispensers comprising an aerosol vial equipped with conventional dispensing valves, preferably metered dose valves, can be used to deliver formulations of the invention. Conventional dispensers and aerosol vials can be used to contain a formulation of the invention. However it has been found that certain vials enhance the chemical stability of certain formulations of the invention. Therefore it is preferred to contain a formulation of the invention within a glass aerosol vial or a metal, in particular aluminum, vial having an interior surface coated with a non-metal coating. A suitable non-metal coating can include a plasma deposited coating such as a diamond like glass coating. Another suitable non metal coating can include a polymer coating, in particular a fluorocarbon polymer coating. Such coatings are known in the art and are described, for example in U.S. Pat. Nos. 8,430,097; 8,414,956; 8,616,201; 8,104,469; and U.S. Patent Application Publication Nos. 2013/0019863, 2013/0025592, and 2011/0103330; which are all incorporated herein by reference in their entirety. Advantageously other internal surfaces, in particular such surfaces of components of the valve, or all of the internal surfaces of the dispenser may be also coated with a polymer, in particular a fluorocarbon polymer. Suitable fluorocarbon polymers include fluorocarbon polymers, which are made of multiples of one or more of the following monomeric units: tetrafluoroethylene (PTFE), fluorinated ethylene propylene (FEP), perfluoroalkoxyalkane (PFA), ethylene tetrafluoroethylene (ETFE), vinylidenefluoride (PVDF), and chlorinated ethylene tetrafluoroethylene. Polymers, which have a relatively high ratio of fluorine to carbon, such as perfluorocarbon polymers e.g. PTFE, PFA, and FEP, are preferred; FEP is particularly preferred.

The valve may be any suitable metering valve with an outlet made from, for example, stainless steel, acetal, nylon or polybutylene terephthalate and with seals made from nitrile or EPDM elastomer.

A pharmaceutical composition prepared according to any process of the present disclosure can be administered to the respiratory tract by oral or nasal inhalation. Oral inhalation is preferred, and conventional actuators for oral inhalation can be used in connection with a pharmaceutical composition made according to a process of the present disclosure. It has been found that good respirable doses are achieved with an orifice diameter within the range of 0.2 to 0.6 mm, preferably in the range 0.30 to 0.50 mm, most preferably 0.35 to 0.45 mm.

FIG. 2 shows one embodiment of a system 2000 that can be used to practice an embodiment of a method according to the present disclosure. The system 2000 comprises a first vessel 20 and a second vessel 25 in selective fluidic communication with the first vessel via two valves (valves 51 and 52, respectively). Also in selective fluidic communication with the first vessel 20 is a vapor addition vessel 45, which supplies vapor-state propellant (e.g., HFA-227, HFA-134A, or mixtures thereof) to the first vessel 20. The vapor addition vessel 45 is selectively isolated from the first vessel 20 via a plurality of valves (valves 58, and 61, respectively).

The second vessel 25 and vapor addition vessel 45 can be supplied with propellant from a propellant reservoir 30. The propellant reservoir 30 is selectively isolated from the vapor addition vessel 45 via a plurality of valves (valves 53 and 61, respectively) and is selectively isolated from the second vessel 25 via a plurality of valves (valves 53 and 54, respectively).

The first vessel 20 is in selective fluid communication with a filler 40, which is configured to deliver the resulting substantially homogeneous pharmaceutical composition (not shown) from the first vessel 20 into a canister (not shown) to be used in a drug-delivery device (e.g., a metered-dose inhaler device). The pharmaceutical composition is transferred from the first vessel 20 to the filler 40 (e.g., by a pump 50). During use, the propellant reservoir 30 is used to deliver liquid-state propellant to the second vessel 25 (to which the first excipient (i.e., the low-molecular weight PEG polymer) is added) and to deliver liquid-state and/or vapor-state propellant to the vapor addition vessel 45. The vapor addition vessel 45 is used to add vapor-state propellant to first vessel 20. After the excipient mixture is prepared in the second vessel 25 according to the present disclosure, the excipient mixture is transferred to the first vessel 20, where it is mixed with at least one pharmaceutically-active compound to make suspension (e.g., a homogeneous suspension) of the pharmaceutical composition. Optionally, additional liquid phase propellant can be added to first vessel 20 through valve 58 after some or all of the excipient mixture has been added to first vessel 20 in order to achieve the proper final concentrations of the pharmaceutically-active agent and the solubilized excipient(s) in the pharmaceutical composition. After the suspension of the pharmaceutical composition is prepared in the first vessel 20, at least a portion of the pharmaceutical composition is transferred (e.g., pumped) to the filling unit 40 where the suspension is used to fill canisters for drug-delivery devices (e.g., metered-dose inhalers).

In any embodiment, the contents of the first vessel 20 can be transferred to a larger vessel (not shown) into which additional liquid-state propellant can be added to achieve the final concentration of suspended pharmaceutically-active compound for use in a metered dose inhaler.

Certain embodiments of the methods of the present disclosure are set forth in the following list of embodiments.

EMBODIMENTS

Embodiment A is method, the method comprising:
transferring a predetermined quantity of an excipient mixture from a second vessel to a first vessel;
wherein the excipient mixture transferred from the second vessel comprises a liquid-state second quantity of a hydrofluoroalkane propellant and a first solubilized excipient;
wherein the first solubilized excipient comprises a low-molecular weight poly(ethylene oxide) polymer;
wherein, before transferring the excipient mixture, the first vessel contains a vapor-phase first quantity of the hydrofluoroalkane propellant and an effective amount of at least one pharmaceutically-active compound; and
contacting the compound with the excipient mixture under conditions that facilitate forming an intermixture comprising the propellant, the first solubilized excipient, and the at least one pharmaceutically-active compound.

Embodiment B is the method of Embodiment A, wherein forming the intermixture comprises forming a pharmaceutical composition.

Embodiment C is the method of Embodiment A or Embodiment B, wherein the method further comprises mixing a liquid-state third quantity of the hydrofluoroalkane propellant with the intermixture to form a pharmaceutical composition.

Embodiment D is the method of any one of the preceding Embodiments wherein, before transferring the excipient mixture, the first vessel is substantially free of liquid-state propellant in fluid contact with the at least one pharmaceutically-active compound.

Embodiment E is the method of any one of the preceding Embodiments, wherein the hydrofluoroalkane propellant is selected from a group consisting of HFA-227, HFA-134A, and mixtures thereof.

Embodiment F is the method of any one of the preceding Embodiments, wherein the low-molecular weight poly(ethylene oxide) polymer has a weight average molecular weight of about 200 Daltons to about 3000 Daltons.

Embodiment G is the method of Embodiment F, wherein the low-molecular weight poly(ethylene oxide) polymer has a weight average molecular weight of about 800 Daltons to about 2000 Daltons.

Embodiment H is the method of Embodiment F, wherein the low-molecular weight poly(ethylene oxide) polymer has a weight average molecular weight of about 1000 Daltons.

Embodiment I is the method of any one of the preceding Embodiments, wherein the excipient mixture comprises about 0.01 weight percent to about 25 weight percent of the poly(ethylene oxide) polymer.

Embodiment J is the method of Embodiment I, wherein the excipient mixture comprises about 0.05 weight percent to about 15 weight percent of the poly(ethylene oxide) polymer.

Embodiment K is the method of Embodiment I, wherein the excipient mixture comprises about 0.1 weight percent to about 10 weight percent of the poly(ethylene oxide) polymer.

Embodiment L is the method of any one of the preceding Embodiments, wherein the pharmaceutical composition comprises about 0.01 weight percent to about 3.0 weight percent poly(ethylene oxide) polymer.

Embodiment M is the method of Embodiment L, wherein the pharmaceutical composition comprises about 0.05 weight percent to about 0.5 weight percent poly(ethylene oxide) polymer.

Embodiment N is the method of Embodiment L, wherein the pharmaceutical composition comprises about 0.3 weight percent poly(ethylene oxide) polymer.

Embodiment O is the method of any one of the preceding Embodiments, wherein the excipient mixture further comprises a second solubilized excipient.

Embodiment P is the method of Embodiment O, wherein the second solubilized excipient comprises a polyvinylpyrrolidone polymer.

Embodiment Q is the method of Embodiment P, wherein the polyvinylpyrrolidone polymer has a K-Value of about 15 to 150 according to the K-Value test described in the European Pharmacopoeia, 5th edition.

Embodiment R is the method of Embodiment P, wherein the polyvinylpyrrolidone polymer has a K-Value of about 15 to 80 according to the K-Value test described in the European Pharmacopoeia, 5th edition.

Embodiment S is the method of Embodiment P, wherein the polyvinylpyrrolidone polymer has a K-Value of about 20 to about 40 according to the K-Value test described in the European Pharmacopoeia, 5th edition.

Embodiment T is the method of Embodiment P, wherein the polyvinylpyrrolidone polymer has a K-Value of about 25 according to the K-Value test described in the European Pharmacopoeia, 5th edition.

Embodiment U is the method of any one of Embodiments P through T, wherein the pharmaceutical composition comprises about 0.0001 weight percent to about 0.05 weight percent of the polyvinylpyrrolidone polymer.

Embodiment V is the method of any one of Embodiments P through U, wherein the pharmaceutical composition comprises about 0.0001 weight percent to about 0.0015 weight percent of the polyvinylpyrrolidone polymer.

Embodiment W is the method of any one of Embodiments P through U, wherein the pharmaceutical composition comprises about 0.0003 weight percent of the polyvinylpyrrolidone polymer.

Embodiment X is the method of any one of Embodiments P through U, wherein the pharmaceutical composition comprises about 0.0005 weight percent of the polyvinylpyrrolidone polymer.

Embodiment Y is the method of any one of Embodiments P through U, wherein the pharmaceutical composition comprises about 0.0007 weight percent of the polyvinylpyrrolidone polymer.

Embodiment Z is the method of any one of Embodiments P through U, wherein the pharmaceutical composition comprises about 0.001 weight percent of the polyvinylpyrrolidone polymer.

Embodiment AA is the method of any one of the preceding Embodiments, wherein the at least one pharmaceutically-active compound is selected from a group consisting of formoterol fumarate and hydrates thereof, budesonide, fluticasone propionate, fluticasone furoate, salmeterol xinafoate, mometasone furoate, albuterol sulfate, beclomethasone, ipratropium bromide, tiotropium bromide, ciclesonide, indacaterol, vilanterol, glycopyrrolate, generally long acting beta agonist, steroids, long acting muscarinic agonists, and a combination of any of the foregoing pharmaceutically-active compounds.

Embodiment AB is the method of Embodiment AA, wherein the at least one pharmaceutically-active compound comprises formoterol fumarate dihydrate and budesonide.

Embodiment AC is the method of Embodiment AA, wherein the at least one pharmaceutically-active compound comprises albuterol sulfate.

Embodiment AD is the method of any one of the preceding Embodiments, wherein the at least one pharmaceutically-active compound comprises particles, wherein the particles have an average particle diameter of less than or equal to 10 microns.

Embodiment AE is the method of any one of the preceding claims:
  wherein transferring a predetermined quantity of an excipient mixture from a second vessel to a first vessel comprises placing the first and second vessels in fluid communication;
  wherein, while the first and second vessels are in fluid communication, the first vessel has a first internal pressure and the second vessel has a second internal pressure;
  wherein the first internal pressure is not more than about 210 kPa below the second internal pressure.

Embodiment AF is the method of Embodiment AE, wherein the first internal pressure is not more than about 105 kPa below the second internal pressure.

Embodiment AG is the method of Embodiment AE, wherein the first internal pressure is not more than about 70 kPa below the second internal pressure.

Embodiment AH is the method of Embodiment AE, wherein the first internal pressure is not more than about 35 kPa below the second internal pressure.

Embodiment AI is the method of any one of the preceding Embodiments, further comprising forming the excipient mixture, wherein forming the excipient mixture comprises:
  contacting the poly(ethylene oxide) polymer with the second quantity of the propellant, wherein at least a portion of the poly(ethylene oxide) polymer contacted with the second quantity is solid state poly(ethylene oxide) polymer; and
  heating the propellant.

Embodiment AJ is the method of Embodiment AI, wherein heating the propellant comprises heating the propellant before it is contacted with the poly(ethylene oxide) polymer.

Embodiment AK is the method of Embodiment AI or Embodiment AJ, wherein heating the propellant comprises heating the propellant after it is contacted with the poly(ethylene oxide) polymer.

Embodiment AL is the method of any one of Embodiments A through AH, further comprising forming the excipient mixture, wherein forming the excipient mixture comprises:
  heating the poly(ethylene oxide) polymer; and
  after heating the poly(ethylene oxide) polymer, contacting the poly(ethylene oxide) polymer with the second quantity of the propellant.

Embodiment AM is the method of any one of the preceding Embodiments, further comprising transferring a predefined mass of the intermixture to a vessel that is configured to be used in a metered-dose inhaler.

Embodiment AN is method of any one of the preceding Embodiments, further comprising transferring a predefined mass of the pharmaceutical composition to a vessel that is configured to be used in a metered-dose inhaler.

Embodiment AO is the method of any one of the preceding Embodiments wherein, prior to transferring a predetermined quantity of an excipient mixture from a second vessel to a first vessel, the first vessel and the second vessel are substantially free of an alcoholic solvent.

Embodiment AP is the method of Embodiment AO wherein, prior to transferring a predetermined quantity of an excipient mixture from a second vessel to a first vessel, the first vessel and the second vessel are substantially free of ethanol.

Embodiment AQ is the method of any one of the preceding Embodiments wherein, prior to transferring a predetermined quantity of an excipient mixture from a second vessel to a first vessel, the first vessel and the second vessel are substantially free of a polar co-solvent.

Objects and advantages of this invention are further illustrated by the following examples, but the particular materials and amounts thereof recited in these examples, as well as other conditions and details, should not be construed to unduly limit this invention.

EXAMPLES

The following compositions were prepared using standard methods well known to those skilled in the art. After the compositions were made according to the present disclosure, the compositions were filled into aluminum aerosol canisters having a fluoropolymer coating comprising either an ethylene-tetrafluoroethylene co-polymer (ETFE) or a blend of perfluorinated ethylene propylene co-polymer (FEP) and polyethersulphone (PES). Aerosol canisters were fitted with metering valves obtained from Aptar Pharma (Congers, N.Y.). As observed visually in glass bottles, compositions prepared according to the present invention were in the form of suspensions which were readily dispersed by hand shaking. The suspension stability of each composition was suitable for use with a metered dose inhaler.

TABLE 1

| List of Materials | | |
| --- | --- | --- |
| Name | Chemical name | Source |
| Budesonide | 16,17-(butylidenebis(oxy))-11,21-dihydroxy-, (11-β,16-α)-pregna-1,4-diene-3,20-dione | |
| Formoterol fumarate | rac-(R,R)-N-[2-hydroxy-5-[1-hydroxy-2-[1-(4-methoxyphenyl) propan-2-ylamino]ethyl] phenyl]formamide, fumarate salt, dihydrate | |

TABLE 1-continued

List of Materials

| Name | Chemical name | Source |
|---|---|---|
| PEG 1000 | Polyethylene glycol | |
| PVP K25 | Polyvinylpyrrolidone | |
| HFA-227 | 1,1,1,2,3,3,3-heptafluoropropane | |

Examples 1-2. Preparation of a Pharmacologic Composition Comprising Budesonide and Formoterol Fumarate

TABLE 2

Composition of the MDI formulation made using the process of Examples 1 and 2.

| Component | Example 1 | Example 2 |
|---|---|---|
| Budesonide, micronized | 7.28 g | 7.28 g |
| Formoterol fumarate, micronized | 0.204 g | 0.21 g |
| PEG 1000 | 9.0 g | 9.0 g |
| PVP K25 | 0 g | 0.03 g |
| HFA-227 | 2983.59 g | 2983.56 g |

The micronized Budesonide and Formoterol fumarate were added to a one-gallon (3.785 liters) first vessel (see first vessel 20, FIG. 2), taking care not to introduce any of the powder into an exit port in the vessel. The first vessel was connected to a vapor addition vessel (see vapor addition vessel 45, FIG. 2) and a second vessel (see second vessel 25, FIG. 2). At least one valve between the first vessel and the vapor addition vessel was closed and at least one valve between the first vessel and the second vessel was closed. The vapor addition vessel contained HFA 227.

Solid-state PEG 1000 and PVP K25 were added to the second vessel. About 300 g of HFA 227 was added to the second vessel and the second vessel was sealed. The second vessel was heated to about 30-40° C. until the PEG and PVP were dissolved (approximately 15-30 minutes) to form the excipient mixture, after which the heat source was removed.

A valve was opened to place the first vessel in vapor communication with the vapor addition vessel and the first vessel was slowly pressurized with HFA 227 vapor from the vapor addition vessel, being careful not to disturb the powdered pharmaceutically-active agents. Heat was applied to the vapor addition vessel as needed to maintain a pressure differential between the first vessel and the vapor addition vessel of no greater than about 35 kPa. The first vessel was filled with HFA 227 vapor to a pressure of about 350 kPa, after which all valves between the first vessel and the vapor addition vessel were closed.

Valves were opened to place the second vessel in fluid communication with the first vessel and the liquid in the second vessel was transferred into the first vessel until the entire contents (i.e., the excipient mixture) of the second vessel were transferred. During the entire transfer process, the pressure differential between the second vessel and the first vessel was maintained at less than or equal to about 138 kPa.

The valves were closed and additional HFA 227 was added to the second vessel to rinse/dilute any residue of the excipient mixture that wasn't transferred. The valves were re-opened and the rinse liquid (HFA 227) from the second vessel was transferred into the first vessel. During the entire transfer process, the pressure differential between the second vessel and the first vessel was maintained at less than or equal to about 138 kPa. The rinse process was repeated several times until the first vessel contained the total amount of HFA 227 shown in Table 2, after which all valves were closed. The contents of the first vessel were mixed at about 7500 rpm for about 5 minutes.

After mixing, the substantially-homogeneous pharmaceutical composition in the first vessel was aliquoted into MDI canisters. MDI canisters were pressure-filled with the composition.

Example 3. Preparation of a Pharmacologic Composition Comprising Albuterol Sulfate

TABLE 3

Composition of the MDI formulation.

| Component | Example 3 |
|---|---|
| Albuterol sulfate, micronized | 3.60 g |
| PEG 1000 | 9.0 g |
| PVP K25 | 0.03 g |
| HFA-134a | 2987.37 g |

The composition of Example 3 was prepared using the process described for Examples 1-2.

The uniformity of the suspensions of the compositions made according to Examples 1-4 was assessed visually and appeared satisfactory for use in a metered dose inhaler.

Effect of Process on the Efficiency of Suspending the Pharmaceutically-Active Particles.

Example 4. Preparation of a Pharmacologic Composition Comprising Budesonide and Formoterol Fumarate The composition of Example 4 was prepared using the components listed in Table 4 according to the process described for Examples 1 and 2. After mixing the contents of Vessel 1 to form the intermixture comprising the propellant, the first solubilized excipient, and the pharmaceutically-active compounds, Vessel 1 was drained. 500 milliliters of 100% ethanol was added to vessel 1 and, using a disposable pipette, the walls and mixer shaft were rinsed with the ethanol to dissolve any residue within vessel. An aliquot of the ethanol was tested to quantify budesonide and formoterol fumarate using High Performance Liquid Chromatography. The results are shown in Table 5.

Comparative Example 1. Preparation of a Pharmacologic Composition Comprising Budesonide and Formoterol Fumarate The quantities of budesonide, formoterol fumarate, PEG 1000, and PVP K25 shown in Table 4 were placed into a vessel and the quantity of liquid-state HFA-227 was added to the vessel. The vessel was stirred at an elevated temperature (about 40° C. for approximately 93 minutes) to allow the excipients to dissolve. After the mixing step, the vessel was drained and the residue was analyzed to quantify budesonide and formoterol fumarate as described in Example 4. The results are shown in Table 5.

TABLE 4

Composition of MDI formulations made in
Example 4 and Comparative Example 1.

| Component | Example 4 | Comparative Example 1 |
|---|---|---|
| Budesonide, micronized | 3.60 g | 3.60 g |
| Formoterol fumarate, micronized | 0.21 g | 0.21 g |
| PEG 1000 | 9.0 g | 9.0 g |
| PVP K25 | 0.03 g | 0.03 g |
| HFA-227 | 2987.16 g | 2987.16 g |

TABLE 5

Residual budesonide and formoterol fumarate in vessels. The
results are reported in micrograms per milliliter ethanol.

| | Residual formoterol fumarate dihydrate (µg/mL) | Residual budesonide (µg/mL) |
|---|---|---|
| Example 4 | 2.93 | 78.25 |
| Comparative Example 1 | 4.69 | 126.07 |

The results show that the active ingredients are suspended more efficiently while using the inventive process than while using a conventional process for preparing a pharmacologic composition. Thus, the method of the present disclosure results in less deposition (i.e., loss) of the active ingredients onto the surface of the mixing vessel than conventional processes.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

The invention claimed is:

1. A method of making a pharmaceutical composition, the method comprising:
adding at least one pharmaceutically active compound to a first vessel;
adding a first quantity of a hydrofluoroalkane propellant to the first vessel, wherein the first quantity of the hydrofluoroalkane propellant is a vapor, to create a first mixture in the first vessel, the first mixture comprising the first quantity of the hydrofluoroalkane propellant and the at least one pharmaceutically active compound; wherein the hydrofluoroalkane propellant is in a vapor phase with less than 5% of the hydrofluoroalkane propellant in a liquid phase based on the total mass of the first mixture; and
transferring an excipient mixture from a second vessel into the first vessel such that an intermixture comprises the excipient mixture and the first mixture formed in the first vessel; the excipient mixture comprising:
a second quantity of the hydrofluoroalkane propellant, wherein the hydrofluoroalkane propellant is liquid;
a poly(ethylene oxide) polymer having a molecular weight from 200 to 3000 Daltons; and
a mass of polar co-solvent before transferring of no more than 1% of the total mass of the pharmaceutical composition.

2. The method of claim 1, wherein the intermixture is suitable for delivery to a patient from a metered dose inhaler.

3. The method of claim 1, wherein less than 1% of the hydrofluoroalkane propellant is in the liquid phase based on the total mass of the first mixture.

4. The method of claim 1, wherein the method further comprises adding additional liquid hydrofluoroalkane propellant to the intermixture after transferring from the second vessel to the first vessel.

5. The method of claim 1, wherein the hydrofluoroalkane propellant is selected from the group consisting of HFA-227, HFA-134A, and a mixture thereof.

6. The method of claim 1, wherein the excipient mixture comprises about 0.01 weight percent to about 3 weight percent of the poly(ethylene oxide) polymer.

7. The method of claim 6, wherein the pharmaceutical composition comprises about 0.01 weight percent to about 3.0 weight percent poly(ethylene oxide) polymer.

8. The method of claim 1, wherein the excipient mixture further comprises a polyvinylpyrrolidone polymer.

9. The method of claim 1, wherein the at least one pharmaceutically-active compound is selected from the group consisting of formoterol fumarate, hydrates of formoterol fumarate, budesonide, fluticasone propionate, fluticasone furoate, salmeterol xinafoate, mometasone furoate, albuterol sulfate, beclomethasone, ipratropium bromide, tiotropium bromide, ciclesonide, indacaterol, vilanterol, glycopyrrolate, beta agonist, steroids, muscarinic agonists, and a combination of any of the foregoing pharmaceutically-active compounds.

10. The method of claim 1, wherein the at least one pharmaceutically-active compound comprises formoterol fumarate dihydrate and budesonide.

11. The method of claim 1, wherein the at least one pharmaceutically-active compound comprises albuterol sulfate.

12. The method of claim 1, wherein the at least one pharmaceutically-active compound comprises particles, wherein the particles have an average particle diameter of less than or equal to 10 microns.

* * * * *